United States Patent
Lim et al.

(10) Patent No.: US 7,604,805 B2
(45) Date of Patent: Oct. 20, 2009

(54) PROTEIN LOGIC GATES

(75) Inventors: Wendell Lim, San Francisco, CA (US); John Dueber, San Francisco, CA (US); Brian Yeh, San Francisco, CA (US)

(73) Assignee: Regents of the University of California, Oakland, CA (US)

( * ) Notice: Subject to any disclaimer, the term of this patent is extended or adjusted under 35 U.S.C. 154(b) by 1120 days.

(21) Appl. No.: 10/613,380

(22) Filed: Jul. 3, 2003

(65) Prior Publication Data

US 2005/0004347 A1 Jan. 6, 2005

(51) Int. Cl.
*A61K 39/00* (2006.01)
(52) U.S. Cl. .................................. 424/192.1
(58) Field of Classification Search .................... 702/19, 702/20
See application file for complete search history.

(56) References Cited

OTHER PUBLICATIONS

Cummingham et al. "Optimizing synthesis and expression of transmembrane peptides and proteins," Methods, vol. 41 (2007) pp. 370-380.*
Kim, "Expression and purificaion of recombinant immunotoxin-a fusion protein stabilizes a single-chain Fv (scFv) in denaturing condition," Protein Expression and Purification, vol. 27 (2003), pp. 85-89.*
Baker et al. "Protein Structure Prediction and Structural Genomics," Science, vol. 294 (2001) pp. 93-96.*
Seffernick et al. "Melamine Deaminase and Atrazine Chlorohydralase: 98 percent identical but functionally different," Journal of Bacteriology, vol. 183 (2001) p. 2405-2410.*
Clark, "Protien refolding for industrial processes," Current Opinion in Biotechnology, vol. 12 (2001) pp. 202-207.*
Pedalacq et al., "Engineering soluble proteins for structural genomics," vol. 20 (2002) pp. 927-932.*
Dueber et al., "Reprogramming Control of an Allosteric Signaling Switch Through Modular Recombination," Science, 2003 vol. 301, pp. 1904-1908.*

* cited by examiner

*Primary Examiner*—Lori A Clow
*Assistant Examiner*—Anna Skibinsky
(74) *Attorney, Agent, or Firm*—Richard Aron Osman

(57) ABSTRACT

Protein logic gates are made from autoregulated fusion proteins comprising an output domain and a plurality of input domains, wherein at least one of the input domains is heterologous to the output domain, and the input domains interact with each other to allosterically and external, ligand-dependently regulate the output domain. The output domain may be constitutively active, and in the absence of the ligand, the input domains interact to inhibit the output domain. The activity of the output domain is user discretionary, and may include activities that are catalytic, label-generative, metabolic-regulative, apototic, specific-binding, etc. Multiple input domains can cooperatively regulate the fusion protein in a wide variety of functionalities, including as an OR-gate, an AND-gate, and an AND-NOT-gate. The gates may be incorporated into cells and therein used to modulate cell function.

3 Claims, No Drawings

PROTEIN LOGIC GATES

This work was supported by Federal Grant No. GM55040 from NIH, and No. EIA-0218256 from NSF. The government may have rights in any patent issuing on this application.

INTRODUCTION

1. Field of the Invention

The invention is in the field of creating synthetic logic gates with fusion proteins.

2. Background of the Invention

A major goal in bioengineering is to create designer cells with novel input/output properties. Such rewired cells would have many practical applications, such as inexpensive but sophisticated biosensors. Also, they would serve therapeutic applications including the repair or reconstruction of defective biological function.

Cells are known to contain protein-based signaling circuits that allow stimuli to be processed and transduced into an appropriate cellular response. These circuits resemble those found in electronic devices: individual proteins in signaling pathways are functionally analogous to electronic logic gates (AND, OR, XOR, etc.) with an output activity that is activated only upon stimulation with the appropriate combination of inputs. Just as electronic logic gates can be wired together to generate an infinite diversity of complex circuits, cells use sets of these protein switches to generate their diverse control circuits. Thus, new cellular behaviors could be generated by rewiring protein switches in novel ways Nonetheless, efforts to rewire cellular circuits are limited by our inability to make protein switches that can link novel inputs and outputs. Electronic logic gates can be connected by simple wiring because they are all controlled by the common input/output currency of flowing electrons. Signaling proteins have no such common currency: they are controlled by diverse inputs including protein, peptide, or small molecule ligands and covalent modification. Moreover, proteins can have extraordinarily diverse catalytic output activities.

Here we describe a new, biologically-inspired strategy that can be used to link protein input and output functions that are normally not related. This strategy provides protein signaling switches analogous to logic gates with diverse and novel input/output properties.

SUMMARY OF THE INVENTION

We have developed a general strategy for introducing novel regulatory control over protein activities. We covalently fuse an unregulated, typically catalytic "output" domain to one or more "input" protein interaction domains and their ligands in a manner such that the intramolecular interactions act to conformationally or sterically inhibit the function of the output domain, a state referred to as "autoinhibition". Under basal conditions the output of the output domain is down-regulated; however, in the presence of one or more external stimuli, such as competitive ligands or covalent modifications that disrupt the autoinhibitory interactions, the output domain is de-repressed and the output activity is up-regulated.

This strategy of generating protein switches has many advantages. First, our strategy is generalized to a wide-range of unrelated input stimuli and output activities because it involves recombination of independent, modular input and output domains; input molecules only act indirectly on the output domain, typically by disrupting auto-inhibitory interactions. Regulation of the output domain is achieved via its stereochemical relationship with the tethered regulatory domain and its intramolecular interactions. Regulation, therefore, does not require making any mutational changes directly within any catalytic region of the output domain. In contrast, prior attempts to engineer ligand-gated allosteric proteins involve making mutations in the starting catalytic domain itself (Ababou, et al. *Protein Sci* 10, 301-12, 2001; Marvin, et al. *Nat Struct Biol* 8, 795-8, 2001). Success with this approach has been limited because it requires an in-depth understanding of the dynamic structures of proteins and an ability to predict how mutations will alter conformational flexibility and ligand binding. Emphasis has been placed on regions that exhibit large conformational changes upon ligand binding (Mizoue, et al. *Curr Opin Struct Biol* 12, 459-63, 2002). Successful mutations must both impair catalytic activity, and allow ligand binding to conformationally induce catalytic activity. Moreover, because it requires making specific amino acid changes directly in the catalytic domain, the design process will be highly case-dependent; successful engineering of one protein activity will likely not translate into success with another, unrelated activity. In contrast, our method of engineering switch proteins is fully generalized.

A second advantage of our strategy is that it provides for the construction of switches that display control by multiple inputs, a requirement for complex switches such as AND-gates (i.e. switches that require the simultaneous presence of two inputs). Because of the modular framework, incorporating multiple input domains in autoinhibition can yield multiple input switches. Attaining multiple input control by directly modifying a single catalytic domain would be much more difficult to achieve.

A third advantage of switches generated by our strategy is that because the protein input and output domains are normally utilized in cellular signaling, they easily interface with and modulate the natural circuitry of cells. To date, most work on engineering novel molecular circuits and switches has been limited to nucleic acids: RNA-based switches, known as allosteric ribozymes. Soukup and Breaker (Soukup, et al., *Proc Natl Acad Sci USA* 96, 3584-9, 1999; Breaker, *Curr Opin Biotechnol* 13, 31-9, 2002) have reported an engineered ribozyme in which ligand-binding to an RNA hairpin can regulate activity of a RNA catalytic domain coupled by a structural linker. Binding of ligand causes structural reorganization of the linker that influences the conformation of the catalytic domain. Although RNA molecules have proven to be a good system for rapidly engineering modular logic gates, a major drawback is that ribozymes are capable of significantly fewer catalytic activities than proteins. Thus, proteins represent the most useful tool for the ultimate goal of engineering desirable circuits in living cells. Our method is ideal for interfacing with biological signaling pathways because it involves novel coupling between input and output domains that are normally used in these processes.

A great deal of work in engineering genetic circuits has also been described over the last few years (Elowitz, et al. *Nature* 403, 335-8, 2000; Guet, et al. *Science* 296, 1466-70, 2002; Yokobayashi, et al. *Proc Natl Acad Sci USA* 99, 16587-91, 2002). These circuits are constructed by recombining transcriptional promoters with genes encoding repressors or activators of downstream promoters. However, because these circuits operate through transcription and translation, they can ultimately only control the levels of protein expression, and not protein activity itself directly. Moreover, they cannot operate at the fast timescales normally associated with protein-based cell signaling circuits. In contrast, switch proteins designed by our method provide the most flexible and rapid approach for re-engineering biological signaling circuits for therapeutic or biotechnological purposes.

The ability to rapidly and flexibly synthesize designer switch proteins offers many advantages. Synthetic switches provide remarkable tools for spatially and temporally controlling protein activity, and inform on many disease mechanisms. The switches may be used to re-engineer cells into biosensors of infectious or toxic agents; for example wherein repressed catalytic labels are activated by the presence of the diagnostic agent. The switches can also be used therapeutically; for example, wherein repressed apoptotic enzymes promote cell death (apoptosis) induced by tumor cell antigens. Additionally, engineered cells can be used for ex or in situ regulated biosynthesis or pathway engineering; for example, a glucose-sensitive switch can be used to activate insulin secretion.

Our invention provides methods and compositions for constructing and using protein switches with novel input/output properties. These switches may operate as sensors, actuators and/or effectors, and may be used in isolation or expressed or incorporated in engineered cells. In one embodiment, our strategy starts with a constitutively active output domain, to which we covalently tether protein interaction domains in such a manner that the intramolecular interactions between the interaction domains inhibit the activity of the output domain. In a particular embodiment, the interaction domains are provided as specific binding pairs which function as receptors and their cognate ligands. Alternatively, a single tethered interaction domain can be used wherein the output domain provides a cognate ligand, typically remote from, so as to not interfere with any catalytic or binding region. For the switch to work, repression can take place by any number of mechanisms (e.g. conformational, steric, etc.). Repression is then relieved by the addition of competing external ligands or other stimuli (e.g. phosphorylation) that disrupt the intramolecular interactions.

Accordingly, the invention provides artificial, autoregulated fusion proteins comprising an output domain and a plurality of input domains, wherein at least one of the input domains is heterologous to the output domain, and the input domains interact with each other (preferably directly) to allosterically and external, ligand-dependently regulate the output domain.

In particular embodiments, the output domain is constitutively active and in the absence of the ligand, the input domains interact to inhibit the output domain. The activity of the output domain is user discretionary, and may include activities that are catalytic, label-generative, metabolic-regulative, apoptotic, specific-binding, etc. In particular embodiments, at least one of the input domains is not heterologous to the output domain, and is remote from and does not interfere with the activity of the output domain.

In particular embodiments, the plurality comprises two input domains, both heterologous to the output domain, and which form a specific binding pair, and the ligand (competitively, allosterically) disrupts pair-specific binding of the input domains. In particular embodiments, the plurality comprises four input domains, all heterologous to the output domain, and which form first and second specific binding pairs which allosterically regulate the output domain dependent on first and second, different external ligands, respectively. Multiple input domains can cooperatively regulate the fusion protein in a wide variety of functionalities, including as an OR-gate, an AND-gate, and an AND-NOT-gate.

The invention also provides methods for modulating the output of the subject fusion proteins comprising the step of contacting the fusion protein with the ligand, whereby the output of the fusion protein is modulated, and optionally, further comprising the step of detecting the modulation of the output of the fusion protein.

The invention also provides cells comprising the subject fusion proteins, particularly cells that naturally utilize the component input domains, and methods for modulating the output of the fusion protein of such cells comprising the step of contacting the fusion protein of the cell with the ligand, whereby the output of the fusion protein is modulated, and optionally, further comprising the step of detecting the modulation of the output of the fusion protein.

DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or.

The invention provides novel autoregulated fusion proteins: artificial, non-natural proteins comprising an output domain and a plurality of input domains, wherein at least one of the input domains is heterologous to the output domain, and the input domains interact with each other, preferably directly, to allosterically and external, ligand-dependently regulate the output domain.

The fusion proteins are allosterically regulated by binding of an external signaling ligand at a site remote from the output domain(s)'s active site. Binding of external signaling ligand(s) is sufficient to regulate the input domains' regulation of the output domain(s), and does not require altering association with any associated external proteins, distinguishing systems requiring an external protein for regulation, such as in steroid ligand binding domain fusions regulated by steroid-dependent association with an inhibitory chaperone.

Autoregulation may be effected by creating allostery de novo using two or more heterologous regulatory input modules, or by exploiting a regulatory domain endogenous to the output domain, in conjunction with one or more heterologous regulatory input modules to provide novel allostery. Hence, the autoregulation may be actuated through alternative mechanisms, such as a tethered pseudosubstrate that directly occludes the active domain, or tethered pairs of binding domains and their cognate ligand motifs, wherein intramolecular interaction of this domain-ligand pair or sets of domain-ligand pairs conformationally regulates the active domain, wherein external ligand binding alters these interactions, whereby the activity of the active domain is allosterically regulated.

The output domain is discretionary according to the intended use, and essentially any output domain providing a desired activity or binding affinity may be employed, so long as output activity can be regulated by ligand-dependent interaction of the input domains. Output domain functional compatibility with the fusion proteins is readily confirmed in activity screens as exemplified below. A wide variety of output activities may be obtained, depending on the ultimate user application, and we have validated the general mechanism across diverse output activities, including catalytic, label-generative, metabolic, apoptotic, and specific-binding activities. For example, output domains may be conveniently selected from the enormous variety of natural, modular catalytic domains or well-known, semi-synthetic engineered or derivitized modular catalytic domains. Table 1 provides a summary of validated output domains.

TABLE 1

Validated output domains

1. Protein Kinase A, such as ERK, Rsk, Cdk (cyclin dependent kinases) and Raf.
2. Tyrosine Kinases, such as Src, Hck, Abl, Zap70 and EGFR-cytoplamic domain.
3. Tyrosine Phosphatases, such as PTP-1 and Shp1.
4. Lipid Kinases, such as Phosphoinositide-3-kinase.
5. Lipid Phophatases, such as PTEN and SHIP.
6. Guanine nucleotide exchange factor, such as catalytic domain from Sos, PH/DH modules, Intersectin, Tiam-1, and Db1.
7. GTPase activating proteins (GAP), such as rho-GAP and ras-GAP.
8. Motor proteins, such as kinesin and Ncd.
9. DNA binding proteins, such as homeodomains and zinc fingers.
10. Transcription activating domain, such as VP16.
11. RNA binding proteins, such as U1A and HIV tat basic peptide.
12. Proteases, such as caspase protease domain.
13. Nuclear localization signals (NLS).
14. Ubiquitin mediated degradation modules (degron).

The switches are readily designed or screened such that external ligand activation up-regulates, down-regulates, or otherwise alters output activity. For example, activation can increase, decrease or alter label expression, binding or substrate affinity or specificity, etc. In particular embodiments, the output domain is constitutively active or functional, and in the absence of the ligand, the input domains interact to inhibit the output domain. Where the selected output domain also comprises a suitable input or interaction domain, this endogenous interaction domain my be exploited to create novel allostery in conjunction with a heterologous input or interaction domain. Typically, such endogenous input domains are positioned on the output domain so as to not interfere with the output activity, e.g. the output activity when the fusion protein is de-repressed with ligand.

The selection of input domains is user discretionary, so long as the selected domains interact to provide the requisite ligand-dependent gating of the output domain. Input domain functional compatibility (demonstrating gating behavior) with the fusion proteins is readily confirmed in activity screens as exemplified below. A wide variety of input may be obtained, depending on the ultimate user application, and we have validated gating behavior across diverse input genuses, including peptide hormones and cognate receptor ligand binding domains (LBD), immune receptors and cognate antigenic peptides, src-homology domains and cognate peptide ligands, and various catalytic input domains, including modular proteases and both cleavable and non-cleavable pseudosubstrate peptides, modular kinases and peptide substrates, modular phosphotases and phospho-peptide substrates, etc. The input domain interaction can be provided by homo- or hetero-dimerization, by specific pair binding, by higher order complex formation, by enzyme-substrate catalysis (e.g. phosphorylation, glycosylation, prenylation, acylation, lipid modification, etc.).

To promote their interactions, one or more of the input domains may be coupled to the fusion protein through a linker or spacer peptide. Linker peptides are widely used in fusion proteins. Linker sequence and length are user-discretionary, though the linkers should not interfere with the ouput domain when the switch is in the active state (e.g. de-repressed), which is readily confirmed empirically. Preferred linkers often provide structural flexibility and mobility to the input domain. Exemplary use of linker peptides is provided in the examples below.

Preferred input domains comprise native, modular interacting domains which mediate binding of naturally interacting proteins, or natural, modular receptors or enzymes and their cognate ligands and substrates. A wide variety of such modular interacting components has been identified, categorized and subject to grafting. In addition, suitable input domains may be derived from vast public databases of known interacting proteins, including Database of Interacting Proteins (DIP), Database of Ligand-Receptor Proteins, Java-based DIP, and LiveDIP; see, e.g. Xenarios, et al. (2002) NAR 30:303-5; Xenarios, et al.(2001) NAR 29:239-41; Xenarios et al., (2000) NAR 28:289-91; Deane et al.(2002) Mol Cell Prot 1:349-356; Graeber et al. (2001) Nat. Genet. 29:295-300; Marcotte et al. (2001) Bioinformatics 17:359-63; Salwinski et al. (2003) Mol Cell Proteomics. 2002 May; 1(5):349-56; Xenarios et al. (2001) Curr Opin Biotechnol 12:334-339. In addition, many protein interaction domains can be mutated to provide alternative specificity binding partners. For example, mutation of a threonine residue of the Src SH2 domain to tryptophan converts ligand-binding specificity from the Src-like pTyr-Glu-Glu-Ile (SEQ ID NO:1), to the signature Grb2 binding motif pTyr-X-Asn (Kimber et al. Molecular Cell 2000. 5, 1043-1049). Table 2 provides a summary of exemplified and validated input domain pairs.

TABLE 2

Exemplary input domain pairs.

1. Src-homology 2 (SH2) domains bind phospho (pY)-containing peptide motifs such as pTyr-Glu-Glu-Ile (SEQ ID NO:1).

| | |
|---|---|
| phosphatidylinositol 3-kinase SH2 domain | IRS-1 (Y608) peptide: Lys-Lys-His-Thr-Asp-Asp-Gly-Tyr($PO_3H_2$)-Met-Pro-Met-Ser-Pro-Gly-Val-Ala (SEQ ID NO:2) |
| human SRC SH2 domain | pp60$^{c-src}$ C-terminal phosphoregulatory peptide: Thr-Ser-Thr-Glu-Pro-Gln-Tyr($PO_3H_2$)-Gln-Pro-Gly-Glu-Asn-Leu (SEQ ID NO:3) |
| Src family members including Src, Lck, and FynSH2 domains | aminocaproyl-Tyr($PO_3H_2$)-Glu-Glu-Ile (SEQ ID NO:1) |

2. Phosphotyrosine binding (PTB) domains bind Asn-Pro-X-Tyr (SEQ ID NO:4) motifs.

| PTB Domain Protein | Binding Partner and Peptide Ligase |
|---|---|
| Shc docking protein | TrkA Nerve Growth Factor Receptor: Ile-Ile-Asn-Pro-Gln-pTyr (SEQ ID NO:5) |

TABLE 2-continued

Exemplary input domain pairs.

IRS-1 docking protein  Insulin receptor: Leu-Tyr-Ala-Ser-Ser-Asn-Pro-Glu-pTyr (SEQ ID NO:6)

X11 neuronal protein  b-amyloid precursor protein: Tyr-Glu-Asn-Pro-Thr-Tyr (SEQ ID NO:7)

3. FHA domains, or forkhead associated domains, mediate phosphopeptide interactions with proteins phosphorylated by serine/threonine kinases.

| FHA domain proteins | Binding partner |
| --- | --- |
| Rad53 Yeast Ser/Thr Kinase | Rad9 (phosphorylated) Yeast checkpoint control protein |
| KAPP Ser/Thr Phosphatase | pRLK5 (phosphorylated) Arabidopsis receptor-like Ser/Thr Kinase |

4. WW domains bind Pro-rich sequences.

| WW domain protein | Binding partner | WW Domain Binding Site |
| --- | --- | --- |
| Yes-Associated Protein (YAP) | Yes (Src-like tyrosine kinase) | PPPPY (SEQ ID NO:8) |
| Nedd4 E3 Ubiquitin Ligase | bENaC amiloride sensitive epithelial Na+ channel E3 Ubiquitin Ligase | PPPNY (SEQ ID NO:9) |
| FBP 11 | Formin | PPLP (SEQ ID NO:10) |

5. 14-3-3 proteins form homo- and hetero-dimeric cup-like structures that bind to discrete phosphoserine-containing motifs.

| 14-3-3 protein | Binding partner |
| --- | --- |
| Mammalian Tau | Cdc25 tyrosine phosphatase |
| Mammalian Epsilon | BAD (Bcl-XL binding partner) |
| Mammalian Tau | c-Raf Ser/Thr Kinase |
| Mammalian Epsilon | PKC Ser/Thr Kinase |
| Mammalian Tau | MEKK1, 2, 3 Ser/Thr Kinase |

6. Src-homology 3 (SH3) domains bind Pro-rich peptides that form a left-handed polyPro type II helix, with the minimal consensus Pro-X-X-Pro (SEQ ID NO:11). Each Pro is usually preceded by an aliphatic residue. Class I and Class 2 SH3 domains recognize RKXXPXXP (SEQ ID NO:12) and PXXPXR (SEQ ID NO:13) motifs, respectively.

| SH3 domain protein | Binding partner | SH3 domain binding site |
| --- | --- | --- |
| Src tyrosine kinase | p85 subunit of PI 3-kinase | RPLPVAP (SEQ ID NO:14) Class I N-terminal to C-terminal binding sit |
| Crk adaptor protein | C3G guanidine nucleotide exchanger | PPPALPPKKR (SEQ ID NO:15) Class II C-terminal to N-terminal binding site |
| FYB (FYN binding protein) | SKAP55 Adaptor protein | RKGDYASY (SEQ ID NO:16) unconventional |
| Pex13p (integral peroxisomal membrane protein) | Pex5p - PTS1 receptor | WXXQF (SEQ ID NO:17) unconventional |

7. Death domains (DD) heterodimerize with the Death domains of distinct proteins, including adaptor proteins such as FADD.

| TNF Receptors | Adaptors |
| --- | --- |
| Fas, TRAIL R1 | FADD |

TABLE 2-continued

Exemplary input domain pairs.

| | |
|---|---|
| Fas | RIP |
| TNF-R55 | TRADD |

8. Death-effector domains (DED) recruit procaspases into complexes with members of the TNF-receptor superfamily. This recruitment is mediated by a homotypic interaction between the procaspase DED and a second DED in an adaptor molecule that is directly associated with activated TNF receptors.

| Caspase | Homotypic Binding partner |
|---|---|
| Pro-caspase-8 | FADD adaptor protein |
| Flame-1 (aka FLIP, I- FLICE, Usurpin etc.) caspase activation inhibitor | FADD adaptor protein |

9. Caspase recruitment domains (CARDs) mediate the association of adaptor proteins and procaspases through heterodimerization of the respective CARDs, recruiting procaspases to upstream signaling complexes and allowing autoactivation.

| CARD protein | Caspase CARD binding partner |
|---|---|
| RAIID Adaptor protein | Pro-Caspase 2 |
| APAF-1 Binds Cytochrome C and dATP | Pro-Caspase 9 |
| CARDIAK Ser/Thr Kinase | Pro-Caspase 1 |

10. Bromodomains have been shown to specifically interact with peptides containing acetylated lysine residues. Recognition of acetyl-lysine is similar to that of acetyl-CoA by histone acetyltransferases.

| BROMO domain proteins | Binding partner |
|---|---|
| P/CAF | acetyl-lysine containing peptides |

11. Chromatin organization modifiers (Chromo) bind chromatin

| Chromodomain proteins | Binding partner |
|---|---|
| HP1 | Histone H3 methylated lysine-9 |

12. Shadow Chromo Domains (CSD) form stable dimers, and dimerization generates an interaction pit that allows docking with partner proteins containing an extended hydrophobic pentapeptide motif.

| CSD proteins | Binding partner |
|---|---|
| Swi6 | homotypic interaction |
| HP1 | Ku70, Su(var)3-7 |

13. F-box domains mediate interaction with Skp1, which links F-box proteins to a core ubiquitin-ligase complex composed of Rbx1, cdc53/Cul1 and the E2 conjugating enzyme cdc34. The C-terminal region of F-box proteins are also composed of various modular domains that interact with target substrates, often phosphorylation dependently.

| F-box domain proteins | F-box Binding partner | C-Terminal Binding partner |
|---|---|---|
| Cdc4 (Yeast) | Skp1, Rbx1 | Sic1 CDK inhibitor |
| Grr1 (Yeast) | Skp1, Rbx1 | Cyclin (CLN) 1, 2 |
| TrCp (Yeast) | Skp1, Rbx1 | IkB(NFkB regulator) |

14. HECT domains, short for Homologous to the E6-AP Carboxyl Terminus bind specific E2s, accept ubiquitin from the E2 to form a ubiquitin-thioester intermediate with the HECT active cysteine, and then transfer ubiquitin to either the e-amino groups of lysine side chains of the substrate or to the growing end of multi-ubiquitin chains.

TABLE 2-continued

Exemplary input domain pairs.

| HECT proteins | E2 Binding partner |
|---|---|
| E6AP | UbcH7 |
| Nedd4 | UbcH5 |
| HectH7 | UbcH7 |
| HectH6 (p532) | UbcH5 |

15. RING fingers bind two atoms of zinc, and mediate protein-protein interactions.

| RING proteins | Binding partner |
|---|---|
| Cbl | UbcH7 |
| RAD5 | UBC13-MMS2 complex |
| RAD6 | RAD18 |
| HHARI | UbcH7 |

16. PDZ domains bind to the C-terminal 4-5 residues of target proteins, frequently transmembrane receptors or ion channels. The consensus binding sequence contains a hydrophobic residue, commonly Val or Ile, at the very C-terminus. PDZ domains can also heterodimerize with PDZ domains.

| PDZ domain protein | Binding partner | Binding Site |
|---|---|---|
| Post-synaptic Density protein 95 (PSD-95) | NMDA receptor B via PDZ1 and PDZ2 of PSD-95 | IESDV-COOH (SEQ ID NO:18) |
| Post-synaptic Density protein 95 (PSD-95) | Kv11.4 (Shaker-type K+ channel) via PDZ1 and PDZ2 of PSD-95 | VETDV-COOH (SEQ ID NO:19) |
| Post-synaptic Density protein 95 (PSD-95) | neural Nitric Oxide Synthase (nNOS) via PDZ2 | PDZ/PDZ interaction |

17. SAM (Sterile Alpha Motif) domains mediate protein-protein interaction via the formation of homo and hetero-typic oligomers.

| SAM domain protein | Binding partner |
|---|---|
| Polycomb group chromatin remodelling proteins: Scm, ph, Rae28 | Homotypic and heterotypic interactions |
| Ste11 Yeast MAPKKK | Ste50 |
| Tel ETS family transcription factor | Tel |

18. Glycine-tyrosine-phenylalanine, or GYF, domains bind to a PPPPGHR (SEQ ID NO:20) proline-rich peptide sequence in the CD2 tail region.

| GYF domain proteins | Binding partner | GYF domain binding site |
|---|---|---|
| CDBP2 | CD2 | PPPPGHR (SEQ ID NO:20) |

19. SNARE (soluble NSF attachment protein (SNAP) receptors) domains enter into a coiled-coil interaction with other SNARE proteins and act as protein-protein interaction modules in the assembly of a SNARE protein complex.

| SNARE complex | SNARE domain proteins in complex |
|---|---|
| Rat synaptic fusion SNARE complex | type1 TGF-b receptor BMPR-I group of receptors ALK1 group of receptors |
| Yeast exocytic post-Golgi SNARE complex | Snc2, Sso1, Sec9 |
| Rat endosomal SNARE complex | Syntaxin 7, Vti 1b, Syntaxin 8 |

TABLE 2-continued

Exemplary input domain pairs.

20. VHS (Vps27p, Hrs and STAM) domains bind to an acidic di-leucine motif in the cytoplasmic domain of sorting receptors including the mannose 6-phosphate receptor.

| VHS proteins | Binding partner |
|---|---|
| GGA | di-leucine motif in the cytoplasmic tail of mannose-6-phosphate receptor |
| Hrs | Hrs FYVE domain |

21. ANK repeats mediate protein-protein interactions.

| ANK repeat protein | Binding partner |
|---|---|
| 53BP2 (p53 binding protein) | p53 |
| p16(INK4a,d) CDK inhibitor | CDK6 |
| GABPalpha Transcription factor | GABPbeta-DNA |

22. Armadillo (ARM, the homolog of mammalian b-catenin) repeats mediate protein-protein interactions.

| ARM domain proteins | Binding partner |
|---|---|
| importin alpha Nuclear import protein | arginine and lysine residues commonly found in nuclear localization signal sequences. |
| beta-Catenin adhesion regulator; transcription factor | APC tumor supressor |

23. WD40 repeats can bind phosphorylated serine and threonine containing peptides.

| WD domain protein | Binding partner |
|---|---|
| G protein B-chain | G protein A, γ-chain |
| Prp4 splicing factor | Prp3 splicing factor |
| cdc4 | phosphorylated Sic 1 |
| Tup1 Transcriptional Repressor | Alpha2 Transcriptional Repressor |

24. LIM domains are zinc binding, cysteine rich motifs consisting of two tandemly repeated zinc fingers, and mediate protein-protein interactions.

| LIM domain proteins | Binding partner | LIM domain binding site |
|---|---|---|
| Enigma | Insulin receptor via third LIM domain of Enigma | tyrosine-containing tight turn in Insulin receptor |
| Enigma | Ret receptor via second LIM domain of Enigma | AKLY (SEQ ID NO:21) motif of Ret receptor |
| PINCH | Integrin linked kinase (ILK) via first LIM domain of PINCH | ANK repeat region of ILK |
| hCRP | hCRP via LIM domains | LIM domain homo-dimerization |

25. MH2 domains of R-Smads mediate the interaction with the Smad binding domain (SBD) of SARA. SARA recruits R-Smads to the type I TGFb receptor, stabilized by an interaction between the MH2 domain and the cytoplasmic domain of the type I TGFb-R. The MH2 of the co-Smad, Smad4, mediates homo-oligomerization of Smad4 trimers and hetero-oligomerization between Smad4 trimers and Smad2 trimer disks.

| MH2 domain proteins | Binding partner |
|---|---|
| Smad1 (R-Smad) | type 1 TGF-b receptor BMPR-I group of receptors ALK1 group of receptors |

TABLE 2-continued

Exemplary input domain pairs.

| | |
|---|---|
| Smad2 (R-Smad) | SARA |
| Smad4 (Co-Smad) | Smad4 to form trimers by homo-oligomerization |

26. Calponin homology (CH) domains in tandem form an F-actin binding region.

| CH Domain Proteins | Binding Partner |
|---|---|
| B-spectrin | F-actin |
| Fimbrin | F-actin |
| Dystrophin | F-actin |

27. Dbl homology (DH) or RhoGEF domains induce Rho family GTPases to displace GDP.

| RhoGEF | Binding Partners |
|---|---|
| Dbl | RhoA/Rac1/Cdc42 |
| p190 RhoGEF | RhoA |
| Tiam-1 | Rac1/Cdc42 |
| p115 RhoGEF | RhoA |

28. Gelsolin homology domain (GEL), also known as gelsolin/severin/villin homology domains, have both calcium binding and actin binding activity, wherein actin binding is calcium regulated.

| GEL Domain Proteins | Binding Partner |
|---|---|
| Gelsolin | $Ca^{2+}$ and F-actin |

29. Phox and Bem1 (PB1) domains are involved in the heterodimerization with a paired PB1 domain. A highly conserved internal sequence known as OPR, PC or AID motifs is necessary for PB1 domain function. Regions outside the OPR, PC and AID help confer specificity for binding.

| PB1 Domain Proteins | Heterodimerization Partners |
|---|---|
| Par-6 isoforms | PKCζ, PKCλ |
| Bem1 | Cdc24 |
| p67$^{Phox}$ | p40$^{Phox}$ |

30. SOCS boxes, or supressors of cytokine signaling family of proteins, target proteins for ubiquitination, and contains the BC-box subdomain that facilitates binding to the Elongin BC complex.

| SOCS Box Domain Proteins | Binding Partners |
|---|---|
| Socs-1 | Elongin B/C |
| Socs-3 | Elongin B/C |

31. RGS (Regulator of G protein Signaling) domains allosterically stabilize the transition intermediate of the GTP binding pocket of the alpha subunit of heterotrimeric G proteins.

| RGS Domain Proteins | Binding Partners |
|---|---|
| RGS-4 | $G\alpha_i$, $G\alpha_q$ |
| p115 RhoGEF | $G\alpha_{12}$, $G\alpha_{13}$ |
| RGS-2 | $G\alpha_q$ |
| GAIP | $G\alpha_i$, $G\alpha_q$ |

TABLE 2-continued

Exemplary input domain pairs.

32. Toll/Il-1 Receptor (TIR) domains mediate
receptor/adaptor oligomerization and association
between receptors and adaptors.

| TIR Domain Proteins | Binding Partners |
|---|---|
| TLR4 | Adaptors (MyD88, TIRAP, Mal), homotypic and possibly heterotypic (Toll-like receptors) interactions |
| MyD88 | Toll-like receptors, IL-1 receptors, homotypic and heterotypic (TIR domain-containing adaptors) interactions |
| Mal | TLR4, MyD88, IRAK-2 and homotypic interactions |

33. Tetratricopeptide repeat (TPR) motif-containing proteins scaffold the assembly of different multiprotein complexes including the anaphase promoting, the peroxisomal import receptor and the NADPH oxidase complexes.

| TPR domain protein | Binding partners | Peptide Ligands |
|---|---|---|
| PEX5 | PTS-1 target signal | S-K-L-COOH |
| Hop | Hsp70 - C-term heptapeptide | E-E-V-D-COOH (SEQ ID NO:22) |
|  | Hsp90 - C- term pentapeptide | E-E-V-D-COOH (SEQ ID NO:22) |
| p67$^{phox}$ | GTP-Rac | surface contacts |

34. TRAF domains interact with activated TNF receptors and IL-1/Toll receptors or through intermediate proteins such as the TRADDs.

| TRAF Domain Proteins | Binding Partners |
|---|---|
| TRAF 1, 2, 3, 5 | CD40 |
| TRAF 1, 2 | TRADD |
| TRAF 6 | IRAK |
| TRAF 2 | TNFR1 |
| TRAF 6 | IL-1 |

35. Ubiquitin-associated (UBA) domains bind mono-, di-, tri-, and tetra-ubiquitin, bind polyubiquitin and can homo and heterodimerize.

| UBA Domain Proteins | Binding Partners |
|---|---|
| HHR23A | mono and polyubiquitin Rad23 (homodimerization) HHR23A (heterodimerization); HIV Vpr |

36. Bcl-2 homology (BH1-4) domains form homodimers and heterodimers between pro and anti apoptotic family members. The N-terminal region, where the BH4 domain resides, interacts with the more distal region of Bcl-2 where BH1, BH2 and BH3 are located. The BH3 domain is required for dimerization and apoptosis induction. Conversely, Bcl-2/Bax heterodimerization requires the BH1, BH2, and BH3 region of Bcl-2 and a central region in Bax where the BH3 domain is located.

| BH1-BH4 domain proteins | Binding partner |
|---|---|
| Bcl-2, Bcl-XL (BH1, BH2, BH3) | Bax, Bad (BH3) |
| Bcl-2 (BH4) | Bcl-2 (BH1, BH2, BH3) |

37. GTPase binding domains/P21 binding domains.

| Binding Domain | Binding Partner |
|---|---|
| WASP GBD | Cdc42 |
| PAK GBD | Cdc42 |
| Ras binding domain (from Raf) | Raf |

A wide variety of external ligands may be used to activate the switches by interacting with one or more of the input domains. The external ligands may activate reversibly, such as by reversible competitive or allosteric interaction with one or more of the input domains, or may activate irreversibly, such as through covalent modification. For example, in the case of an SH3 input domain, proline rich peptides can be used as both a second, integral input domain, and as an external competitive ligand. Alternatively, the external ligand can comprise a kinase activity which phosphorylates (covalently modifying) the SH3 domain proximate to the proline-rich binding site, and thereby disrupts interaction of the input domains.

In particular embodiments, the fusion proteins comprise two input domains, both heterologous to the output domain, and which form a specific binding pair. In these embodiments, the intput domains may also be referred to as receptor-ligand pairs, wherein this internal ligand is one of the input domains, as opposed to the actuating, external ligand which competitively or allosterically disrupts pair-specific binding of the input domains. This input domain binding pair motif may be expanded with additional input domains to provide any desired form of cooperative or antagonistic regulation. For example, the fusion protein may comprise two or more specific binding pairs of input domains which provide higher-order cooperative gating behavior. Accordingly, depending on design or selection, multiple input domains can cooperatively regulate the fusion protein in a wide variety of functionalities, including as an OR-gate, an AND-gate, and an AND-NOT-gate. Similarly, a plurality of output domains can be combined in a single fusion protein, to provide more complex switching. Table 3 provides a summary of validated fusion proteins.

TABLE 3

Validated gated fusion proteins.

| Fusion | Output Domain | Input Domain 1 | Input Domain 2 | External Ligand |
|---|---|---|---|---|
| #PFD12 | PKA (Ser kinase) | FHA domain | PDZ domain | Ser-phosph/C-term peptide |
| #CRS77 | Caspase | Ras binding domain | SH2 domain | Ras/Tyr-phospho-peptide |
| #USP35 | Ubiquitin Degron | SH2 dom | PAK GBD | Tyr-phosphopeptide/Cdc42 |
| #U1S49 | U1A (RNA binding) | 14-3-3 dom | SH3 dom | Ser-phosp/pro-rich peptide |
| #PPW86 | PI3 kinase | PDZ domain | WASP GBD | C-terminal peptide/Cdc42 |
| #DRF42 | Dbl domain | Ras bind domain | FYVE dom | Ras/lipid |

The fusion proteins may be incorporated into higher-order structures, such as macromolecular complexes and cells. Cells comprising the fusion proteins may be used as biosynthetic vehicles, as biosensors, as physiological actuators, etc. The cells may be in any context: isolated, cultured, in situ, etc. In a particular embodiment, cells in situ provide external ligand activatable switches for modulating a physiology of the host. For example, we show that in two distinct transgenic animal models, a genetically disrupted signaling pathway can be functionally rescued by expression and ligand-activation of a transgene encoding a subject fusion protein. In analogous demonstrations, we use rodent tumor models to demonstrate that our regulatable apoptosis (cell death) actuators can function as effective tumor cell-specific therapies. In addition, cells transformed to express our ligand-activatable fusion proteins are able to alter host physiology in animal transplantation models, including synthetic β-cells hosting a ligand-activatable insulin transcriptional activation switch in a diabetic mouse model.

The invention also provides methods for modulating the output of the subject fusion proteins by contacting the fusion protein with the ligand, whereby the output of the fusion protein is modulated. These methods may be preceded by optional steps such as constructing and/or isolating the fusion protein and followed by optional steps such as detecting the modulation of the output of the fusion protein. The fusion protein may be modulated in isolation, or within host macromolecular structures, cells or organisms.

DETAILED EXAMPLE

Eukaryotic signaling proteins can display sophisticated behaviors such as allosteric gating and multi-input signal integration, properties essential for the formation of complex cellular circuits. Most such signaling proteins are built from modular components—independently folding domains with binding or catalytic functions, and it has been hypothesized that this component-based framework may facilitate evolution (1-3). Modular binding domains play two major roles: targeting and regulation. Targeting, the co-recruitment of proteins in a pathway, is a relatively simple function that appears to be interchangeable. For example, scaffold proteins contain multiple binding domains that each recruit specific members of a pathway. In some scaffolds, domain interchange can yield novel assemblies and, correspondingly, novel signaling pathways (4, 5).

Modular interaction domains, however, can also play more complex regulatory roles, participating in autoinhibitory interactions that allosterically gate catalytic activity (3, 6). Src-family kinases (7) contain a kinase domain that in isolation is constitutively active. However, in the intact protein two modular interaction domains, a Src Homology 2 (SH2) domain and a Src Homology 3 (SH3) domain, participate in coordinated intramolecular interactions that lock the kinase domain in an inactive conformation (8, 9). Src kinases therefore act as switches whose activity is triggered by competing intermolecular SH2 and SH3 ligands (7, 10). Similarly, the actin regulatory protein N-WASP (Neuronal Wiskott-Aldrich Syndrome Protein) (11, 12) contains an output region (referred to as "VCA" or "WA" domain) that in isolation is constitutively active—it stimulates actin polymerization by binding and activating the actin-related protein (Arp) 2/3 complex. However, two modular domains, a highly basic (B) motif and a GTPase binding domain (GBD) participate in coordinated autoinhibitory interactions that repress this activity (13, 14). Two activating stimuli, the phosphoinositide PIP2 and the activated GTPase Cdc42, act by binding to the B and GBD motifs, respectively, and disrupting autoinhibition (14, 15). These switch proteins can display quite sophisticated signal integration behavior. For example, activation of N-WASP by Cdc42 and PIP2 is extremely cooperative, thus N-WASP approximates an AND-gate—strong activation is only observed in the presence of both inputs (14, 16). Such behavior is thought to yield precise spatial and temporal control over actin polymerization.

Here we explore the flexibility of modular regulation: we use domain recombination to reprogram input control of the actin polymerization switch, N-WASP. We find that even simple recombination events can yield switches that are precisely gated by heterologous, non-physiological ligands. Moreover, the diversity and complexity of gating behaviors that emerge from a recombination library are comparable to those observed in natural allosteric proteins, and include integration between two previously unrelated inputs.

Constructing a single input switch. To probe whether the gating function of modular binding domains is interchangable, we engineered a simple synthetic signaling switch whose activity was gated by a single heterologous ligand. The logic of our design was to tether an unrelated modular domain-ligand pair to a constitutively active output domain. If activity could be autoinhibited by the heterologous domain-ligand interaction, the construct should act as a switch that could be activated by a competitive, external ligand.

As a core activity, we utilized N-WASP's output domain, which as an isolated domain constitutively activates Arp2/3-mediated actin polymerization (11, 12). This ~100 amino acid domain contains a C-terminal acidic motif that binds Arp2/3 and an N-terminal verprolin homology motif, which binds actin monomers, probably delivering them to Arp2/3 (16, 17). Homologous output domains are found in other Arp2/3 activators such as WAVE/Scar (18). Alone, this domain appears to be relatively unstructured, but its binding to Arp2/3 is required for actin nucleation. As the autoinhibitory module, we utilized a PDZ domain (19). PDZ domains, which mainly recognize specific C-terminal peptides, are found in numerous eukaryotic scaffolding proteins, but are not normally physiologically associated with actin polymerization switches like N-WASP. We constructed our first switch (P1) by linking the PDZ domain from al-syntrophin to the N-terminus of the output region and linking its corresponding peptide ligand, to the C-terminus (20). In principle, this design would lead to an actin polymerization switch that was specifically activated by PDZ ligand peptide.

Activity of switch proteins was determined using a fluorescence-based actin polymerization assay (21). Time required to reach 50% polymerization (t1/2) was used as a metric for activity. Minimal activity was defined as the t1/2 observed with spontaneous actin polymerization under these conditions (in presence of Arp2/3 but no nucleation promoting factors). Maximal activity was defined as the t1/2 in the presence of the constitutively active output domain. Relative activities of individual constructs were scored by measuring the change in t1/2 relative to the difference between maximum and minimum activities.

Activity of the designed PDZ switch (P1) was strongly repressed under basal conditions. Parallel constructs that only contained the N-terminal PDZ domain or the C-terminal PDZ ligand showed no significant repression, indicating that the individual recognition partners alone did not interfere with Arp2/3 stimulation. Moreover, repression was not observed when saturating free PDZ domain (0.5 mM, ~100-fold>Kd of interaction) was added in trans to the construct bearing only the C-terminal PDZ ligand. Thus, autoinhibition was dependent on the intramolecular PDZ interaction.

This synthetic switch is conformationally repressed. The repressed protein can still bind the Arp2/3 complex (22), indicating that inhibition does not occur through simple occlusion of Arp2/3. Moreover, gel filtration studies indicate that inhibition does not involve protein oligomerization (22). We infer that the intramolecular PDZ interaction locks the output domain in an inactive conformation or restricts dynamic properties required for activity.

Most importantly, the designed switch showed the target gating behavior: activation in response to increasing concentrations of free PDZ ligand, with a maximal activity close to that of the isolated output domain. The concentration of activator required for half-maximal activation (Kact) was approximately 50 mM.

Precise gating behavior was dependent on the affinity of the autoinhibitory interaction. Variant switches with internal PDZ ligands of reduced affinity showed lower basal repression, further demonstrating the key role of the PDZ interaction in repression. In addition, these variant switches showed increased sensitivity to activation by external PDZ ligand (reduced Kact).

Constructing a two-input switch library. Many signaling switches can respond to multiple inputs (3). In electronic circuits, multi-input gates (AND, OR, XOR, etc.) are essential for complex signal processing. Similarly, in cellular regulation, multi-input switch proteins are required for complex circuits involving combinatorial control or feedback and feed-forward loops. Thus, our second goal was to use modular recombination to generate synthetic multi-input switches that could integrate the effects of two previously unrelated inputs. Specifically, we targeted the design of a synthetic N-WASP-based switch that, like the native molecule, displayed AND-gate regulation, but in response to novel combinations of inputs. The design strategy was to covalently tether two modular domain/ligand pairs to N-WASP's output domain such that intramolecular interactions might function cooperatively to conformationally repress activity. Such a switch would, in principle, respond cooperatively to the combination of both competing external ligands.

To explore the increased complexity of two-input switches, we generated a library of constructs in which we combinatorially varied switch design parameters including domain type, domain-ligand affinity, linker length, and domain architecture. The output domain of N-WASP was the core activity of the switch, but to increase variability we used a long (residues 392-501) and a short (residues 429-501) version, both of which display constitutive Arp2/3 mediated actin polymerization activity (17).

Switch designs were divided into two main classes. "Chimeric" switches are those in which the targeted behavior was dual regulation by PDZ ligand and Cdc42. These switches were constructed using a PDZ domain and the native N-WASP GBD as regulatory modules. The GBD binds a peptide (the cofilin helix or C, ~residues 461-479) within the N-WASP output region, an interaction that is competitively disrupted by activated Cdc42 (13). Although the intramolecular GBD interaction is required for autoinhibition in native N-WASP, it is not sufficient: the interaction does not repress N-WASP activity unless combined with the autoinhibitory interaction of the B module (the PIP2 responsive element) (14). Thus, in these switches, we are reengineering N-WASP to respond to Cdc42 and PDZ ligand, as opposed to Cdc42 and PIP2, as is observed naturally.

"Heterologous" switches are those in which targeted behavior was dual regulation by PDZ and SH3 domain ligands, two completely non-native inputs. These switches were constructed using PDZ and SH3 domains. SH3 domains recognize short proline-rich motifs (23). Like PDZ domains, SH3 domains are not normally used as autoinhibitory elements in WASP-family switches, although they are used in other unrelated switches such as Src family kinases (1, 7).

In both switch classes, we utilized intramolecular peptide ligands with varying affinities. Domains were linked with Ser-Gly repeat linkers of varying lengths (0 to 20 residues). Finally, input and output domains and their ligands were tethered in a variety of sequences. High affinity intermolecular ligands that compete with intramolecular ligands for binding to the autoinhibitory domains, served as gating inputs.

Screening for multi-input switches. We screened a library of switches for activity in the presence of no inputs, each individual input, and both inputs together. Like most signaling proteins, these modular allosteric switches do not give simple binary responses; the precise response observed depends on the input concentrations used. We performed our activation screens using a standard set of input concentrations: 10 mM Cdc42GTPgS, 200 mM PDZ ligand, 10 mM SH3 ligand. Each of these concentrations is 20 to 100-fold greater than the Kd observed for input ligand binding to its isolated recognition domain.

Switches could be divided into diverse classes based on behavior observed under these standard conditions. At the extremes, 5 switches showed little or no basal repression, while 9 were extremely well-repressed, but could not be activated by these input concentrations. Most constructs, however, showed gating behavior. Of the remaining 20 switches, 16 were positively gated (both inputs activate). Two of the proteins displayed antagonistic gating: one input activates while the other represses. The mechanism of this switch behavior is discussed below.

The positively gated dual input switches could be further subdivided. Two proteins showed OR-gate-like behavior: roughly equivalent activation in the presence of either individual input or both together. Five proteins showed clear AND-gate-like behavior, while the remaining constructs showed intermediate behavior. Thus, this relatively small library yielded a wide diversity of switch behaviors, including several with the targeted AND-gate behavior.

Several design principles are revealed by examining the relationship between switch parameters and behavior. As was observed with the single input switches, basal repression and input sensitivity are directly coupled to the affinity of autoinhibitory interactions. For example, the chimeric switch C11, which has an intramolecular PDZ ligand with dissociation constant of 8 mM, is well-repressed under basal conditions but insensitive: it cannot be activated by the standard concentrations of PDZ ligand or Cdc42, even in combination. However, if the intramolecular PDZ ligand affinity is reduced (KPDZ=100 mM), the protein now resembles an AND-gate (switch C12).

Heterologous switch behavior also demonstrated a dependence on modular interaction affinity. For example, switch H15, which has internal SH3 and PDZ ligands with dissociation constants of KSH3=10 mM and KPDZ=100 mM, resembles an OR-gate. However, increasing the affinity of the internal PDZ ligand by ~10-fold (KPDZ=8 mM) within the same architecture yields a well-behaved AND-gate (switch H14). Interestingly, in one architectural context the 8 mM PDZ affinity is too tight to yield AND-gate behavior (switch C11), whereas in another context this affinity is ideal (switch H14). We infer that this is due, in part, to differences in the affinity of the partner domain; in C11 the partner domain is the GBD with a 1 mM affinity for its internal ligand (14, 24), whereas in H14 the partner domain is an SH3 domain with an internal ligand affinity of ~10 mM. Hence, to maintain balance between switch repression and sensitivity we balance the affinities of the highly coupled autoinhibitory interactions.

Linker length can also affect switch behavior. As discussed above, switch H14 resembles an AND-gate, indicative of strong coupling between the PDZ and SH3 input domains. However, if the linkage between the PDZ and SH3 domains is increased from 5 to 20 residues, the switch becomes more sensitive to the isolated inputs, indicative of reduced thermodynamic coupling between these domains. This finding is consistent with observations that coupling between regulatory domains of Src family kinases depends strongly on conformational and energetic features of the interdomain linker (25).

Designed switches can spatially target actin polymerization. The AND-gate behavior of N-WASP is thought to play a key biological role in spatially regulating actin polymerization; polymerization is strongly activated at sites where both Cdc42 and PIP2 are present (14). We examined whether this type of precise spatial gating could be mediated by the synthetic heterologous switch H14, which behaves as an SH3/PDZ ligand dependent AND-gate. To avoid confuision from endogenous SH3 or PDZ ligands, we examined targeted activation in Xenopus oocyte extract. Carboxylated polystyrene beads were coated with Glutathione-S-transferase (GST) fusions to the relevant input ligands: no ligand (GST alone), SH3 ligand, PDZ ligand, or SH3 and PDZ ligands connected in tandem. The latter tandem fusion offered a simple test of the effects of co-localizing both inputs.

The coated beads were incubated with soluble H14 switch and oocyte extract supplemented with rhodamine-labeled actin. Actin filament nucleation, detected by the formation of a fluorescent cloud surrounding the bead, was only observed on beads coated with the tandem SH3-PDZ ligand. Just as native N-WASP appears to be most strongly activated in the presence of co-localized Cdc42 and PIP2, this synthetic switch appears to be selectively activated in the presence of co-localized SH3 and PDZ ligand.

Switch diversity: antagonistic integration. Although this library originally targeted AND-gate behavior, the library yielded switches with the behavior of antagonistic input control (H1, H2). For these switches, SH3 ligand acts as a repressor while PDZ ligand acts as an activator. Stimulation with both ligands yields intermediate activity. Detailed examination of the gating properties of switch H2 in various input concentration regimes reveals that PDZ ligand always acts as an activator; SH3 ligand, however, increases the basal level of repression, essentially increasing the dynamic range of the switch.

The antagonistic regulation observed in this switch is consistent with a simple model in which the intramolecular SH3 and PDZ interactions are anti-cooperative. This behavior would be observed if (1) the intramolecular PDZ interaction is solely responsible for autoinhibition, and (2) the intramolecular SH3 interaction destabilizes the intramolecular PDZ interaction but, by itself, has no direct effect on output activity. We modeled this simple scheme by assuming that the state in which both intramolecular interactions take place is unfavorable and unpopulated. Such a scheme predicts an activation surface that very closely resembles the observed behavior of switch H2. Further support for this model comes from the behavior of variant switches in which the affinity of the internal PDZ ligand was altered. In this series of switches, the maximum level of repression observed (in the presence of SH3 ligand), directly correlated with PDZ affinity. This trend is consistent with repression driven solely by the intramolecular PDZ interaction.

In this type of antagonistic switch, the two domains appear to act in a nested manner: the SH3 intramolecular interaction negatively regulates the PDZ intramolecular interaction, which in turn negatively regulates the output activity. Addition of exogenous SH3 ligand, therefore, favors the autoinhibitory PDZ interaction, leading to the observed inhibitory effect. In contrast, in positive integrating switches that resemble AND-gates, the two domains work in concert to negatively regulate output function. Consequently, disruption of both intramolecular interactions yields activation. This set of switches highlights the power of behavior diversification that can occur with simple recombination events.

Our results demonstrate that multi-domain signaling switches are functionally modular—diverse and complex gating behaviors can be generated through relatively simple recombination events between input and output domains, even among domains with no previous evolutionary relationship. These findings highlight a central difference between what we define as "modular allosteric" proteins and conventional allosteric proteins. The general phenomenon of allosteric gating occurs when a protein can exist in distinct high and low activity conformational states, and regulatory ligands bind and preferentially stabilize one state. In conventional allosteric proteins, input and output activities are centralized in a single folded structure (or homo-oligomer). Gating is mediated by subtle shifts that occur within this structure. Thus conventional allosteric switches appear to be poorly amenable to the evolution of radically different input/output gating relationships.

In contrast, in modular allosteric proteins, the regions that mediate input control are physically separable from output regions. Conformational control of activity is mediated by changes in the structural relationship of these domains. Moreover, in multiple input switches, regions that mediate control by individual inputs are also physically separable. Physical separation permits recombination of input and output domains, leading to diversification of regulatory control over a given output activity; see also 26-34.

REFERENCES

1. T. Pawson, P. Nash, Genes Dev 14, 1027-47 (2000).
2. E. S. Lander et al., Nature 409, 860-921 (2001).
3. W. A. Lim, Curr Opin Struct Biol 12, 61-8 (2002).
4. S. H. Park, A. Zarrinpar, W. A. Lim, Science 299, 1061-4 (2003).
5. J. Tong, S. Elowe, P. Nash, T. Pawson, J Biol Chem 278, 6111-9 (2003).
6. M. A. Pufall, B. J. Graves, Annu Rev Cell Dev Biol 18, 421-62 (2002).
7. F. Sicheri, J. Kuriyan, Curr Opin Struct Biol 7, 777-85 (1997).
8. W. Xu, S. C. Harrison, M. J. Eck, Nature 385, 595-602 (1997).
9. F. Sicheri, I. Moarefi, J. Kuriyan, Nature 385, 602-9 (1997).
10. I. Moarefi et al., Nature 385, 650-3 (1997).
11. R. D. Mullins, Curr Opin Cell Biol 12, 91-6 (2000).
12. H. N. Higgs, T. D. Pollard, Annu Rev Biochem 70, 649-76 (2001).
13. A. S. Kim, et al., Nature 404, 151-8 (2000).
14. K. E. Prehoda, J. A. Scott, R. D. Mullins, W. A. Lim, Science 290, 801-6 (2000).
15. R. Rohatgi, H. Y. Ho, M. W. Kirschner, J Cell Biol 150, 1299-310 (2000).
16. R. Rohatgi et al., Cell 97, 221-31 (1999).
17. J. Zalevsky, L. Lempert, H. Kranitz, R. D. Mullins, Curr Biol 11, 1903-13 (2001).
18. L. M. Machesky et al., Proc Natl Acad Sci USA 96, 3739-44 (1999).
19. B. Z. Harris, W. A. Lim, J Cell Sci 114,3219-31 (2001).
20. J. Schultz et al., Nat Struct Biol 5, 19-24 (1998).
21. R. D. Mullins, L. M. Machesky, Methods Enzymol 325, 214-37 (2000).
22. J. Dueber, unpublished data.
23. B. J. Mayer, J Cell Sci 114, 1253-63 (2001).
24. M. Buck, W. Xu, M. K. Rosen, Biochemistry 40, 14115-22 (2001).
25. M. A. Young, et al., Cell 105, 11526 (2001).
26. J. Monod, J. -P. Changeux, J. Jacob, J Mol Biol 6, 306-29 (1963).
27. S. B. Carroll, Nature 409, 1102-9 (2001).
28. M. Ptashne, A. Gann, Curr Biol 8, R812-22 (1998).
29. C. C. Guet, M. B. Elowitz, W. Hsing, S. Leibler, Science 296, 1466-70 (2002).
30. J. Hasty, D. McMillen, J. J. Collins, Nature 420, 224-30 (2002).
31. W. Winkler, A. Nahvi, R. R. Breaker, Nature 419, 952-6 (2002).
32. W. C. Winkler, S. Cohen-Chalamish, R. R. Breaker, PNAS USA 99, 15908-13 (2002).
33. L. S. Mizoue, W. J. Chazin, Curr Opin Struct Biol 12, 459-63 (2002).
34. M. Huse, J. Kuriyan, Cell 109, 275-82 (2002).

The foregoing descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An autoregulated fusion protein comprising an output domain and a plurality of input domains, wherein at least one of the input domains is heterologous to the output domain, and the input domains interact with each other to allosterically and external ligand-dependently regulate the output domain wherein the output domain is a Neuronal Wiskott-Aldrich Syndrome Protein (N-WASP) WA domain, and the input domains are (i) a PDZ domain and (ii) a SH3 domain.

2. A method for modulating output of the fusion protein of claim 1, the method comprising the step of contacting the fusion protein with the ligand, whereby the output of the fusion protein is modulated.

3. The method of claim 2, further comprising the step of detecting the modulation of the output of the fusion protein.

* * * * *

UNITED STATES PATENT AND TRADEMARK OFFICE
CERTIFICATE OF CORRECTION

PATENT NO. : 7,604,805 B2 Page 1 of 1
APPLICATION NO. : 10/613380
DATED : October 20, 2009
INVENTOR(S) : Wendell Lim, John Dueber and Brian Yeh It is certified that error appears in the above-identified patent and that said Letters Patent is hereby corrected as shown below:

The reservation of government rights at Col. 1, lines 3-5 should read:

This invention was made with government support under Grant Number GM55040 awarded by the National Institutes of Health and Grant Number EIA-0218256 awarded by the National Science Foundation. The government has certain rights in these inventions.

Signed and Sealed this

Twenty-fourth Day of November, 2009

David J. Kappos
*Director of the United States Patent and Trademark Office*

SEQUENCE LISTING

```
<160> NUMBER OF SEQ ID NOS: 22

<210> SEQ ID NO 1
<211> LENGTH: 4
<212> TYPE: PRT
<213> ORGANISM: Artificial
<220> FEATURE:
<223> OTHER INFORMATION: consensus sequence

<400> SEQUENCE: 1

Tyr Glu Glu Ile
1

<210> SEQ ID NO 2
<211> LENGTH: 16
```

```
<212> TYPE: PRT
<213> ORGANISM: Artificial
<220> FEATURE:
<223> OTHER INFORMATION: consensus sequence

<400> SEQUENCE: 2

Lys Lys His Thr Asp Asp Gly Tyr Met Pro Met Ser Pro Gly Val Ala
1               5                   10                  15

<210> SEQ ID NO 3
<211> LENGTH: 13
<212> TYPE: PRT
<213> ORGANISM: Artificial
<220> FEATURE:
<223> OTHER INFORMATION: consensus sequence

<400> SEQUENCE: 3

Thr Ser Thr Glu Pro Gln Tyr Gln Pro Gly Glu Asn Leu
1               5                   10

<210> SEQ ID NO 4
<211> LENGTH: 4
<212> TYPE: PRT
<213> ORGANISM: Artificial
<220> FEATURE:
<223> OTHER INFORMATION: consensus sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 4

Asn Pro Xaa Tyr
1

<210> SEQ ID NO 5
<211> LENGTH: 6
<212> TYPE: PRT
<213> ORGANISM: Artificial
<220> FEATURE:
<223> OTHER INFORMATION: consensus sequence

<400> SEQUENCE: 5

Ile Ile Asn Pro Gln Tyr
1               5

<210> SEQ ID NO 6
<211> LENGTH: 9
<212> TYPE: PRT
<213> ORGANISM: Artificial
<220> FEATURE:
<223> OTHER INFORMATION: consensus sequence

<400> SEQUENCE: 6

Leu Tyr Ala Ser Ser Asn Pro Glu Tyr
1               5

<210> SEQ ID NO 7
<211> LENGTH: 6
<212> TYPE: PRT
<213> ORGANISM: Artificial
<220> FEATURE:
<223> OTHER INFORMATION: consensus sequence

<400> SEQUENCE: 7

Tyr Glu Asn Pro Thr Tyr
1               5
```

```
<210> SEQ ID NO 8
<211> LENGTH: 5
<212> TYPE: PRT
<213> ORGANISM: Artificial
<220> FEATURE:
<223> OTHER INFORMATION: consensus sequence

<400> SEQUENCE: 8

Pro Pro Pro Pro Tyr
1               5

<210> SEQ ID NO 9
<211> LENGTH: 5
<212> TYPE: PRT
<213> ORGANISM: Artificial
<220> FEATURE:
<223> OTHER INFORMATION: consensus sequence

<400> SEQUENCE: 9

Pro Pro Pro Asn Tyr
1               5

<210> SEQ ID NO 10
<211> LENGTH: 4
<212> TYPE: PRT
<213> ORGANISM: Artificial
<220> FEATURE:
<223> OTHER INFORMATION: consensus sequence

<400> SEQUENCE: 10

Pro Pro Leu Pro
1

<210> SEQ ID NO 11
<211> LENGTH: 4
<212> TYPE: PRT
<213> ORGANISM: Artificial
<220> FEATURE:
<223> OTHER INFORMATION: consensus sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 11

Pro Xaa Xaa Pro
1

<210> SEQ ID NO 12
<211> LENGTH: 8
<212> TYPE: PRT
<213> ORGANISM: Artificial
<220> FEATURE:
<223> OTHER INFORMATION: consensus sequence
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 12

Arg Lys Xaa Xaa Pro Xaa Xaa Pro
1               5

<210> SEQ ID NO 13
```

```
<211> LENGTH: 6
<212> TYPE: PRT
<213> ORGANISM: Artificial
<220> FEATURE:
<223> OTHER INFORMATION: consensus sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 13

Pro Xaa Xaa Pro Xaa Arg
1               5

<210> SEQ ID NO 14
<211> LENGTH: 7
<212> TYPE: PRT
<213> ORGANISM: Artificial
<220> FEATURE:
<223> OTHER INFORMATION: consensus sequence

<400> SEQUENCE: 14

Arg Pro Leu Pro Val Ala Pro
1               5

<210> SEQ ID NO 15
<211> LENGTH: 10
<212> TYPE: PRT
<213> ORGANISM: Artificial
<220> FEATURE:
<223> OTHER INFORMATION: consensus sequence

<400> SEQUENCE: 15

Pro Pro Pro Ala Leu Pro Pro Lys Lys Arg
1               5                   10

<210> SEQ ID NO 16
<211> LENGTH: 8
<212> TYPE: PRT
<213> ORGANISM: Artificial
<220> FEATURE:
<223> OTHER INFORMATION: consensus sequence

<400> SEQUENCE: 16

Arg Lys Gly Asp Tyr Ala Ser Tyr
1               5

<210> SEQ ID NO 17
<211> LENGTH: 5
<212> TYPE: PRT
<213> ORGANISM: Artificial
<220> FEATURE:
<223> OTHER INFORMATION: consensus sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 17

Trp Xaa Xaa Gln Phe
1               5

<210> SEQ ID NO 18
<211> LENGTH: 5
<212> TYPE: PRT
```

```
<213> ORGANISM: Artificial
<220> FEATURE:
<223> OTHER INFORMATION: consensus sequence

<400> SEQUENCE: 18

Ile Glu Ser Asp Val
1               5

<210> SEQ ID NO 19
<211> LENGTH: 5
<212> TYPE: PRT
<213> ORGANISM: Artificial
<220> FEATURE:
<223> OTHER INFORMATION: consensus sequence

<400> SEQUENCE: 19

Val Glu Thr Asp Val
1               5

<210> SEQ ID NO 20
<211> LENGTH: 7
<212> TYPE: PRT
<213> ORGANISM: Artificial
<220> FEATURE:
<223> OTHER INFORMATION: consensus sequence

<400> SEQUENCE: 20

Pro Pro Pro Pro Gly His Arg
1               5

<210> SEQ ID NO 21
<211> LENGTH: 4
<212> TYPE: PRT
<213> ORGANISM: Artificial
<220> FEATURE:
<223> OTHER INFORMATION: consensus sequence

<400> SEQUENCE: 21

Ala Lys Leu Tyr
1

<210> SEQ ID NO 22
<211> LENGTH: 4
<212> TYPE: PRT
<213> ORGANISM: Artificial
<220> FEATURE:
<223> OTHER INFORMATION: consensus sequence

<400> SEQUENCE: 22

Glu Glu Val Asp
1
```